United States Patent [19]
Glover

[11] Patent Number: 5,967,947
[45] Date of Patent: Oct. 19, 1999

[54] ISOMETRIC WRIST EXERCISE DEVICE

[76] Inventor: James T. Glover, 17401 E. 41st St., Apt. E, Independence, Mo. 64055

[21] Appl. No.: 09/072,074

[22] Filed: May 4, 1998

[51] Int. Cl.$^6$ .................................................. A63B 21/00
[52] U.S. Cl. ................................ 482/91; 482/44; 482/45
[58] Field of Search .................................. 602/32, 39, 34, 602/40, 21; 482/91, 92, 79, 904, 907, 45, 44, 124

[56] References Cited

U.S. PATENT DOCUMENTS

| | | |
|---|---|---|
| 1,188,711 | 6/1916 | Wilting ....................................... 602/39 |
| 1,556,496 | 10/1925 | Davis ......................................... 602/32 |
| 4,616,637 | 10/1986 | Caspari et al. ............................ 602/39 |
| 5,186,698 | 2/1993 | Mason et al. .............................. 482/92 |
| 5,290,220 | 3/1994 | Guhl ........................................... 602/32 |
| 5,366,436 | 11/1994 | Gibney . | 
| 5,413,553 | 5/1995 | Downes . |
| 5,441,058 | 8/1995 | Fareed . |
| 5,468,220 | 11/1995 | Sucher . |
| 5,478,306 | 12/1995 | Stoner . |
| 5,492,525 | 2/1996 | Gibney . |
| 5,514,052 | 5/1996 | Charles et al. . |
| 5,551,933 | 9/1996 | Washburn . |
| 5,788,607 | 8/1998 | Baker ......................................... 482/44 |

*Primary Examiner*—Jerome Donnelly
*Attorney, Agent, or Firm*—Litman, Kraai & Brown L.L.C.

[57] ABSTRACT

An isometric wrist exercise device which is useful for strengthening the wrist and for treating or alleviating symptoms associated with carpal tunnel syndrome device includes a wrist brace which adjustably encircles a user's wrist. The brace is attached to a swivel plate via a plurality of straps which extend forward from the wrist brace. The swivel plate is attached to an elongate strap with a wedge plate on its opposite end. The wedge plate can secure the elongate strap in a stationary position such that the user can place his wrist in therapeutic traction by pulling his arm against the stationary strap while selectively swiveling his wrist to find the optimum position.

13 Claims, 2 Drawing Sheets

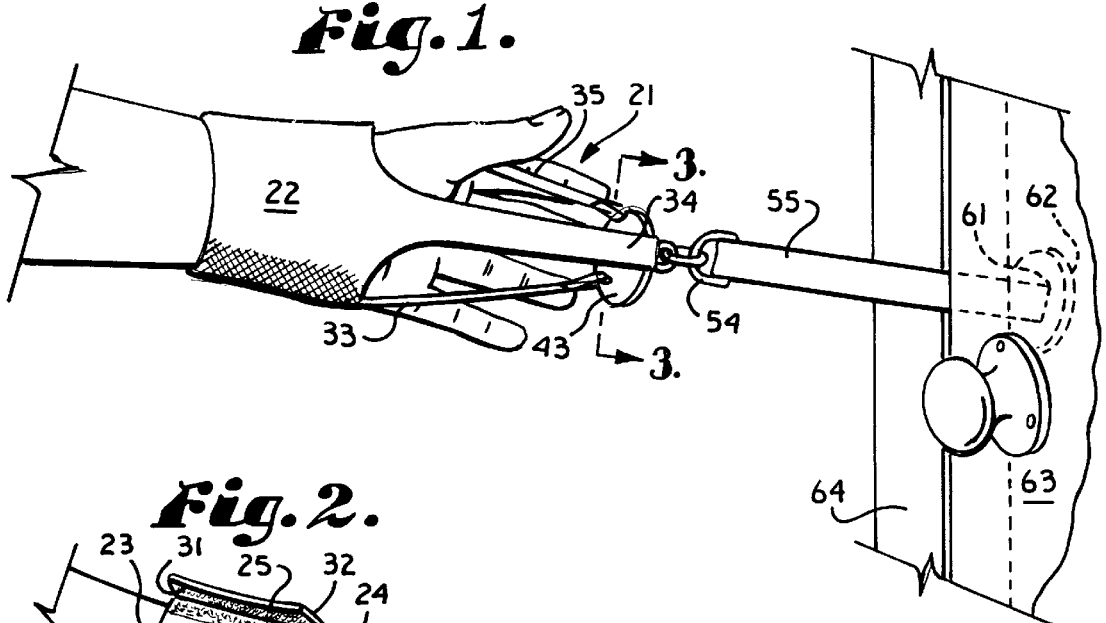
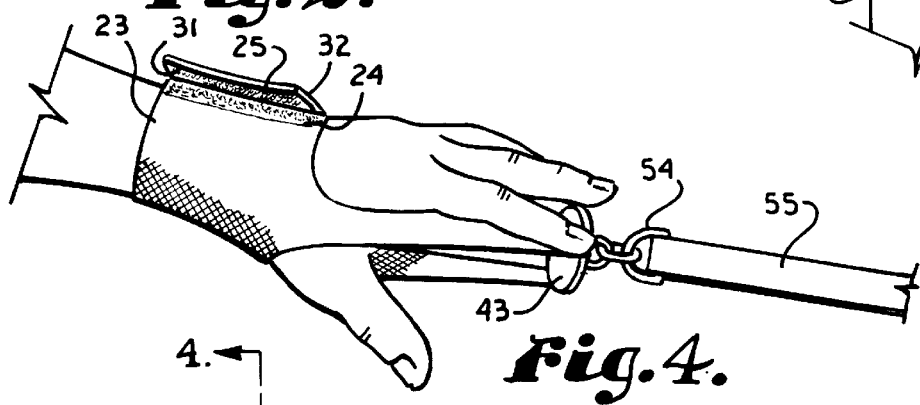
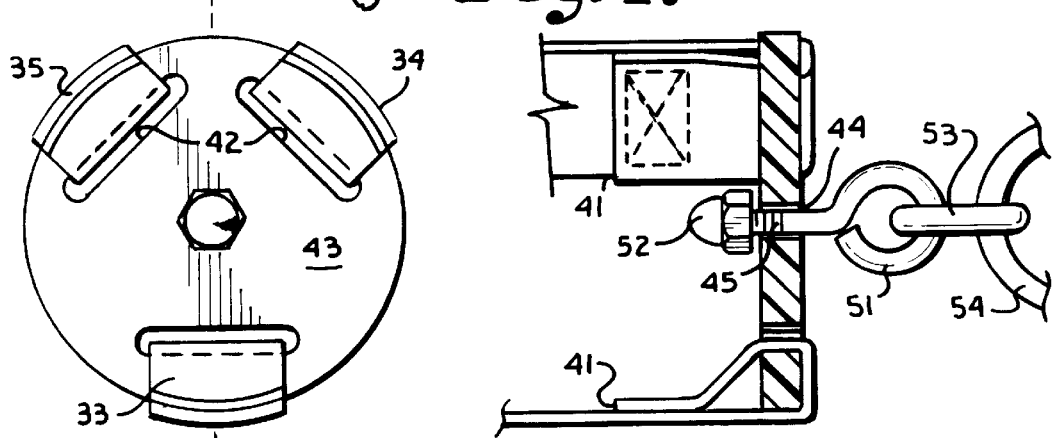

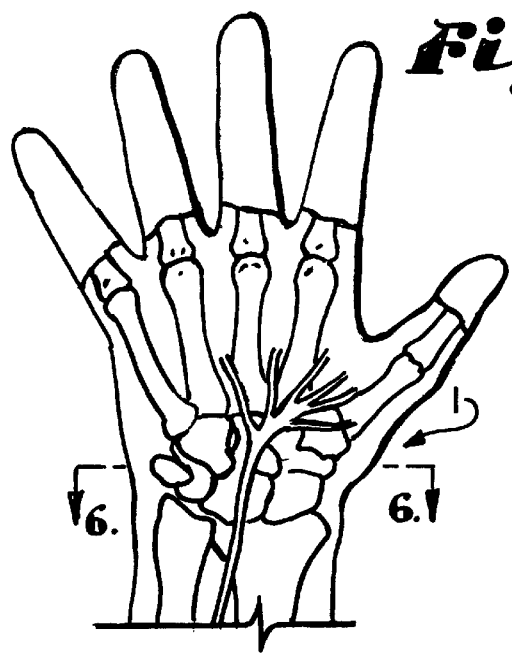
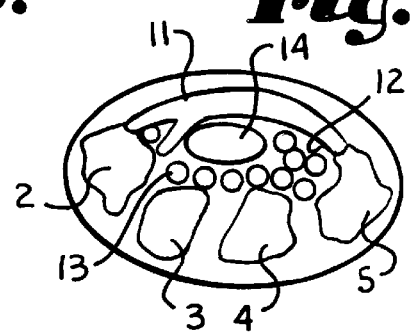
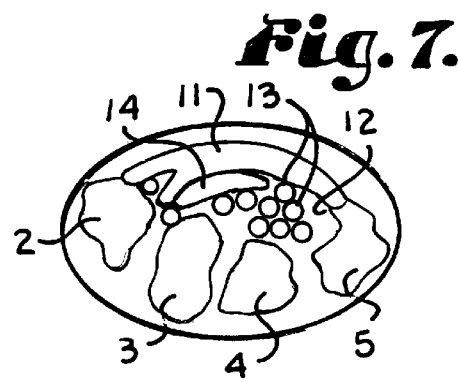
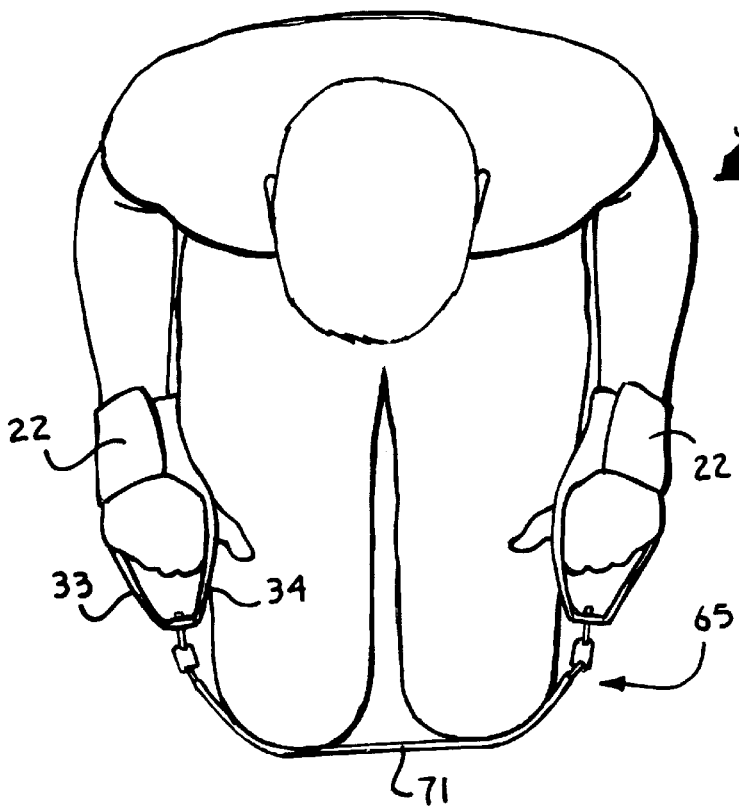

ISOMETRIC WRIST EXERCISE DEVICE

BACKGROUND OF THE INVENTION

1. Field of the Invention

This invention is related to a wrist and hand exercise device, and, more particularly, to such a device which can be used to freely exercise a user's wrist and help to align the carpal bones within the wrist to prevent or help alleviate Carpal Tunnel Syndrome effects.

2. Description of the Related Art

Carpal Tunnel Syndrome (CTS) is a widespread health problem, both in the United States and abroad. With the ever increasing use of computers and computer keyboards in virtually all fields of endeavor, the problem is getting worse all of the time. CTS is one of the leading causes of work related injuries and costs employers billions of dollars annually in lost production time and worker's compensation claims. CTS, and other musculoskeletal disorders were estimated by the U.S. Department of Labor Statistics (BLS) to account for over 60 percent of all work related injuries in the U.S. in 1995, not including back injuries. Furthermore, the number of cases of work related repeated trauma injuries has risen from 23,800 cases in 1972 to 332,000 cases in 1994, a fourteenfold increase. For cases involving days away from work, the BLS estimates that 32%, or 705,800 cases in 1994 were due to overexertion or repeated trauma injuries.

CTS is a repetitive motion injury which can be caused or aggravated by any repetitive flexing and extension action involving a person's wrists, such as, for example, typing or keyboard data entry. The underlying physical cause is the misalignment or fixation of one or more of the eight wrist "carpal" bones which surround the "carpal tunnel". Within this carpal tunnel nine flexor tendons, which control finger movement, and the median nerve, which is a pathway for sensory cells in the hand, pass through the wrist to the hand. When one or more of the carpal bones does not work harmoniously with the others, inflammation and swelling occur which can cause the carpal tunnel ligament to tighten down on the carpal tunnel and put pressure on the median nerve and/or the flexor tendons. A number of physical symptoms can accompany CTS, including pain, numbness, aching, burning and tingling sensations, stiffness, swelling, sensation of swelling where none exists, loss of strength and grip, and clumsiness. Symptoms may start in the hands and wrists and radiate upward to the forearm and shoulder joint. Severe CTS can result in atrophy of the thenar muscle at the base of the thumb and even in total hand and wrist disability.

Medical treatment of relatively mild CTS can include immobilization and rest, the use of ice packs to the affected area and drugs such as anti-inflammatories and diuretics to reduce swelling. Severe CTS is often treated with surgery, with approximately 100,000 operations per year occurring in the U.S. alone. Surgery is an expensive and risky procedure which is often unsuccessful. Full recovery from CTS surgery can take from months to a full year. Surgery can also lead to scarring of the transverse ligament within the wrist, which can further irritate the median nerve, thus causing CTS symptoms to reoccur.

Various therapeutic treatments have been developed for treatment of CTS without resort to surgery and drugs. One such treatment series, used most often by chiropractors, involves a product called the "CTD-Mark1 Pneumatic Traction Device" by ParaTech Industries, Inc. This machine, which costs several thousand dollars, includes a large console which is positioned near a sitting patient. The patient rests her elbow in an L shaped pad and a restraining strap is placed around her bicep while a second restraining strap is placed around her forearm. A third strap is placed around her wrist which third strap is attached to one end of a pair of nylon traction straps. The opposite ends of the nylon traction straps are attached to a rod extending upward out of the console. When operated, a pneumatic piston within the console urges the rod away from the L shaped pad, thus exerting force on the wrist brace in a linear direction, thus placing the patient's wrist into traction. According to the manufacturer's literature, "The resulting controlled extension of the arm and wrist causes a reduction in the compression of the carpal tunnel ligament upon the median nerve. The carpal bones now open to allow more room in the carpal tunnel as a result of the carpal ligament relaxation." Typically, 8–10 treatments are recommended for mild CTS while many more can be required for severe CTS. This can be a very expensive and time consuming experience, with each traction treatment involving a trip to the doctor's office (and accompanying payment).

In addition to the cost and attendant inconvenience of this complicated machine, the machine has some other problems. Since the patient's wrist is entirely immobilized when it is placed under traction, pressure is exerted in a given region of the wrist. However, CTS can be caused by misalignment or calcification of any one or more of the eight wrist bones surrounding the carpal tunnel. Pressure on the wrist in one orientation may be effective for one patient but ineffective for another. It is useful, therefore, for the wrist to be oriented in differing positions while undergoing pressure so that a variety of pressure points can be tried until the patient experiences alleviation of their particular CTS symptoms. With the CTD-MARK1, once the wrist is placed under pneumatic traction, the wrist cannot be turned, thus experimentation "on the fly" to find the best position for pain alleviation is difficult or impossible. Furthermore, the immobilization of the patient's elbow and forearm, and the rigid attachment of the wrist encircling strap to the nylon traction straps also does not permit much variation in traction pressure.

It is clear, then, that a better, and much less expensive wrist exercise and CTS treatment device and method is needed. Such an exercise and treatment device should preferably be inexpensive, yet safe and simple enough to use such that anyone exhibiting the symptoms of CTS can purchase and use the device in their own home without medical supervision. Such a device should allow a user to easily and effectively vary traction pressure on the affected wrist and wrist position in order to find the most effective wrist orientation for symptomatic relief from CTS.

SUMMARY OF THE INVENTION

The present invention is an isometric wrist exercise device which is useful for strengthening the wrist and for treating or alleviating symptoms associated with CTS. The exercise device includes a wrist brace which encircles a user's wrist. The brace is made of a fairly wide web of flexible material with an overlying flap equipped with a hook and loop fastener to allow the brace to be adjusted in size to fit any size of wrist. The wrist brace includes a plurality of straps which extend forward from the wrist brace and each strap has a terminal end which extends through a respective slot in a circular swivel plate and then back over the exterior of the swivel plate and back onto itself where it is secured by sewing, riveting or the like. The swivel plate has a central aperture with a fastener, such as an eye bolt, extending therethrough and secured on a rear side of the swivel plate such that the swivel plate freely swivels relative to the eye bolt. The eye bolt is attached, via one or more links, to one end of an elongate strap. The opposite end of the elongate strap is attached to a wedge plate which can be secured into position between a door and door jamb, for example on an opposite side of the door from a user. With the elongate strap held stationary by the closed door holding the wedge plate in a fixed position, a user, by steadily pulling their arm backward against the wrist brace, can manually exert a traction force against the wrist. The freely swiveling action of the swivel plate allows the user to freely rotate their wrist while exerting pressure, to find the most beneficial position for applying wrist traction to alleviate their particular condition. Repetitive use of the wrist exercise device over a period of time will strengthen the wrist and arm and help to realign any wrist bones which have become misaligned, thus serving to help open up the carpal tunnel and alleviate pressure on the median nerve.

In an alternative embodiment, two wrist exercise devices are linked by a common strap such that a user can put a wrist brace about each wrist, place the common strap about their knees and pull simultaneously on both arms to place both wrists under traction.

Principal Objects and Advantages of the Invention

The principal objects and advantages of the present invention include: providing an improved isometric wrist exercise device; providing such a device which can be used in a home or work environment to strengthen a user's wrist and to alleviate CTS symptoms; providing such a device which is light, portable, and which can be stored in a very small space; providing such a device in which a wrist brace encircles the user's wrist, with the wrist brace being attached to a stationary elongate strap via a swivel plate; providing such a device which allows a user to place traction on their own wrist to help align any misaligned carpal bones and to alleviate pressure on the median nerve within the carpal tunnel; and providing such a device which is efficient and reliable, economical to manufacture and which is particularly well suited to its intended purpose.

Other principal objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of an isometric wrist exercise device in accordance with the present invention, with the device being used to place traction on a wrist and with a traction disc shown in dotted lines on a side of a door opposite the user's position.

FIG. 2 is a fragmentary, perspective view of the isometric wrist exercise device of FIG. 1, showing the wrist brace being swiveled to an alternative position to change the points of application of traction pressure on the user's wrist.

FIG. 3 is an enlarged, rear elevational view of a swivel plate forming part of the exercise device of FIG. 1, taken along line 3—3 of FIG. 1.

FIG. 4 is an enlarged, fragmentary, cross sectional view of a portion of the exercise device showing the swivel plate, eye bolt and strap connections to the swivel plate.

FIG. 5 is a representative illustration of a typical wrist and hand musculoskeletal structure.

FIG. 6 is a cross-sectional view of a portion of the wrist carpal tunnel region, taken along line 6—6 of FIG. 5, and illustrating a normal condition of four carpal bones with the carpal tendon and carpal tunnel intact.

FIG. 7 is another cross-sectional view of the same portion of the wrist carpal tunnel region, again taken along line 6—6 of FIG. 5, and illustrating a CTS condition where the median nerve is being constricted by the carpal tendon.

FIG. 8 is a top view of an alternative embodiment of the isometric wrist exercise device, showing a user with a wrist exerciser on each respective wrist, and with a connecting common strap encircling the user's knees to allow him to exert traction on both wrists simultaneously.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "front", "rear", "right" and "left" will refer to directions in the drawings to which reference is made.

Referring to the drawings in more detail, FIGS. 5, 6 and 7 illustrate a typical musculoskeletal structure of a wrist and hand. The area of interest is the wrist carpal area, generally indicated at 1. In the carpal area 1, two layers of four carpal bones 2–5 are interconnected by a large carpal tendon 11. The carpal bones 2–5 and the tendon 11 surround a region known as the "carpal tunnel" 12 through which nine flexor tendons 13 and a median nerve 14 extend to the hand. FIG. 6 shows a normal carpal tunnel 12 with an unrestricted area for the median nerve 14 and the flexor tendons 13, as shown by the ample space surrounding the median nerve 14. By contrast, FIG. 7 illustrates a wrist of a person with CTS where the carpal bone 3 is misaligned, resulting in swelling and compression of the median nerve 14 and compression of some or all of the flexor tendons 13 between the bone 3 and the carpal tendon 11. This compression of the median nerve 14 and/or the flexor tendons 13 can cause some or all of the CTS symptoms described earlier.

FIGS. 1–4 illustrate an isometric wrist exercise device, generally indicated at 21, which is useful for strengthening the wrist and for treating or alleviating symptoms associated with CTS. The exercise device 21 includes a wrist brace 22 with an outer surface 23, a portion of which has attached thereto the hook or loop portion 24 a hook and loop fastener system with a mating portion 25 being attached to an inner surface 31 of a flap 32. The wrist brace can thus be placed about a user's wrist and adjusted and held in the position shown by use of the mating hook and loop fastener portions 24 and 25.

A plurality of straps 33–35 are attached to and extend forward from the wrist brace 22 and each of the straps 33–35 has a terminal end 41 which extends through a respective slot 42 arrayed circumferentially about a swivel plate 43.

Each terminal strap end 41 is then doubled back over the periphery of the swivel plate 43 and is attached, as by sewing, back to the strap itself to hold it in place on the swivel plate 43. The swivel plate 43 has a center through bore 44 through which a threaded shaft 45 of an eye bolt 51 is extended. The bore 44 is preferably slightly oversized to allow the swivel plate 43 to freely swivel about the shaft 45. A nut 52, which is preferably nylon lined, is threaded onto the end of the shaft 45 to maintain the eye bolt 51 in position. The eye bolt 51 is attached, via one or more links 53, to a loop 54 on one end of an elongate strap 55. It should be noted that the illustrated swivel attachment is representative only, and there are other methods of attachment of the swivel plate 43 to the elongate strap 55 which could be equally effective.

An opposite end 61 of the elongate strap 55 is attached to a wedge plate 62. The wedge plate 62 is sized to be positioned on an opposite side of a door 63 between the door 63 and the door jamb 64 to keep the wedge plate 62 in a stable position.

With the elongate strap 55 thus secured in position by the closed door 63, a user, by pulling their arm backward against the wrist brace 22, can manually exert a traction force against the wrist. The freely swiveling action of the swivel plate 43 allows the user to freely rotate their wrist while exerting pressure, as indicated by the different wrist positions shown in FIGS. 1 and 2, respectively, to find the most beneficial position for applying wrist traction to alleviate their particular condition, i.e. to align the particular misaligned one or ones of the carpal bones 2–5. Repetitive use of the wrist exercise device 21 over a period of time will strengthen the wrist and arm and help to realign any carpal bones 2–5 which have become misaligned, thus serving to help open up the carpal tunnel 12 and alleviate pressure on the median nerve 14.

In an alternative embodiment of wrist exercise device shown in FIG. 8, and generally indicated at 65, two wrist braces 22 are connected to respective swivel plates 43 via straps 33–35 in the same manner described above. The swivel plates 43 are then attached to respective opposing ends of a common strap 71. A user can thus exercise both wrists by placing a respective one of the wrist braces 22 about each wrist and positioning the common strap 71 about their knees. By then simultaneously pulling on both arms, the user can place both wrists under traction.

Various changes to the invention will occur to those skill in the art. For example, the wrist brace 22 can be attached to the swivel plate 43 via more or less than the 3 straps 33–35 shown. The swivel plate 43 can be attached to the elongate strap 55 by any alternative swivel connection, e.g. a bearing or the like. The wedge plate 62 can be any desired shape of size or it can be replaced with a hook and eye or other means of retaining the elongate strap in position for the user to pull against. It is thus to be understood that while certain forms of the present invention have been illustrated and described herein, it is not to be limited to the specific forms or arrangement of parts described and shown.

I claim:

1. An isometric wrist exercise device, comprising:
    a) a wrist brace, said wrist brace including a web having a length sufficient to encircle a user's wrist and having a width sufficient to extend a substantial distance above and below the wrist so as to encompass the carpal bones of the user;
    b) an elongate strap;
    c) a swivel mechanism attached to the elongate strap such that the wrist brace is free to swivel relative to the strap; and
    d) at least three connecting straps spaced circumferentially about said wrist brace with each connecting strap being connected at one end to the wrist brace and at an opposite end to said swivel mechanism.

2. An isometric wrist exercise device as in claim 1, and further comprising:
    a) a securing mechanism which is attached proximate a terminal end of said elongate strap to secure said elongate strap in place such that a user can exert traction on their wrist by pulling their arm away from said elongate strap.

3. An isometric wrist exercise device as in claim 2, said securing mechanism comprising a wedge plate attached to said terminal end of said elongate strap.

4. An isometric wrist exercise device as in claim 1, said wrist brace further comprising:
    a) a first portion of a hook and loop fastener attached to an outer surface of said web; and
    b) a second, mating portion of said hook and loop fastener secured to an inner surface of said web to thereby secure said web snugly about a user's wrist.

5. An isometric wrist exercise device as in claim 1, wherein said swivel mechanism includes:
    a) a swivel plate with said opposite ends of each of said connecting straps being attached to said swivel plate and spaced circumferentially therearound; and
    b) an eye bolt extending through a center aperture in said swivel plate, said eye bolt being attached to said elongate strap.

6. An isometric wrist exercise device, comprising:
    a) a wrist brace, said wrist brace including a web having a length sufficient to encircle a user's wrist and having a width sufficient to extend a substantial distance above and below the wrist so as to encompass the carpal bones of the user;
    b) an elongate strap;
    c) at least three connecting straps spaced circumferentially about said wrist brace with each connecting strap being connected at one end to the wrist brace and at an opposite end to said elongate strap and
    d) a securing mechanism which is attached proximate a terminal end of said elongate strap to secure said elongate strap in place in a position such that a user can exert traction on their wrist by pulling their arm away from said elongate strap.

7. An isometric wrist exercise device as in claim 6, and further comprising:
    a) a swivel mechanism attached between the connecting straps and to the elongate strap such that the wrist brace is free to swivel relative to the strap.

8. An isometric wrist exercise device as in claim 7, wherein said swivel mechanism includes:
    a) a swivel plate with said opposite ends of each of said connecting straps being attached to said swivel plate and spaced circumferentially therearound; and
    b) an eye bolt extending through a center aperture in said swivel plate, said eye bolt being attached to said elongate strap.

9. An isometric wrist exercise device as in claim 6, said wrist brace further comprising:
    a) a first portion of a hook and loop fastener attached to an outer surface of said web; and
    b) a second, mating portion of said hook and loop fastener secured to an inner surface of said web to thereby secure said web snugly about a user's wrist.

10. An isometric wrist exercise device, comprising:
a) a wrist brace including:
   i) a web, said web having a length sufficient to encircle a user's wrist and having a width sufficient to extend a substantial distance above and below the wrist so as to encompass the carpal bones of the user;
   ii) a first portion of a hook and loop fastener attached to an outer surface of said web; and
   iii) a second, mating portion of said hook and loop fastener secured to an inner surface of said web to thereby secure said web snugly about a user's wrist;
b) an elongate strap;
c) a securing mechanism which is attached proximate a terminal end of said elongate strap to secure said elongate strap in place in a position such that a user can exert traction on their wrist by pulling their arm away from said elongate strap;
d) at least three connecting straps spaced circumferentially about said wrist brace with each connecting strap being connected at one end to the wrist brace and at an opposite end to a swivel mechanism such that the wrist brace is free to swivel relative to the strap, said swivel mechanism including a swivel plate with said opposite ends of each of said connecting straps being attached to said swivel plate and spaced circumferentially therearound.

11. An isometric wrist exercise device as in claim 10, wherein said swivel mechanism includes:
a) an eye bolt extending through a center aperture in said swivel plate, said eye bolt being attached to said elongate strap.

12. An isometric wrist exercise device as in claim 11, wherein said swivel mechanism includes:
a) a swivel plate attached to said wrist brace via a plurality of straps; and
b) an eye bolt extending through a center aperture in said swivel plate, said eye bolt being attached to said elongate strap.

13. An isometric wrist exercise device as in claim 11, said securing mechanism comprising a wedge plate attached to said terminal end of said elongate strap.

* * * * *